United States Patent [19]
Bush et al.

[11] Patent Number: 5,385,578
[45] Date of Patent: Jan. 31, 1995

[54] ELECTRICAL CONNECTION FOR MEDICAL ELECTRICAL STIMULATION ELECTRODES

[75] Inventors: M. Elizabeth Bush, Fremont; Drew Hoffmann, Los Gatos; M. Dean Matthews, Saratoga; Pedro G. Medrano, Santa Clara, all of Calif.

[73] Assignee: Ventritex, Inc., Sunnyvale, Calif.

[21] Appl. No.: 18,832

[22] Filed: Feb. 18, 1993

[51] Int. Cl.⁶ ............................................. A61N 1/00
[52] U.S. Cl. .............................................. 607/122
[58] Field of Search ........................ 607/119–122, 607/116–118, 123, 125–132, 154, 156; 128/642; 606/32, 41

[56] References Cited

U.S. PATENT DOCUMENTS

| | | | |
|---|---|---|---|
| 4,161,952 | 7/1979 | Kinney et al. | 128/786 |
| 4,214,804 | 7/1980 | Little | 128/419 |
| 4,314,095 | 2/1982 | Moore et al. | 128/419 |
| 4,328,812 | 5/1982 | Ufford et al. | 128/786 |
| 4,355,646 | 10/1982 | Kallok et al. | 607/122 |
| 4,458,695 | 7/1984 | Peers-Trevarton | 128/786 |
| 4,662,382 | 5/1987 | Sluetz et al. | 128/785 |
| 4,679,572 | 7/1987 | Baker, Jr. | 128/786 |
| 4,784,161 | 11/1988 | Skalsky et al. | 128/785 |
| 4,827,932 | 5/1989 | Ideker et al. | 128/419 |
| 4,844,099 | 7/1989 | Skalsky et al. | 128/785 |
| 4,917,106 | 4/1990 | Olivier | 607/120 |
| 4,940,065 | 7/1990 | Tanagho et al. | 607/118 |
| 4,945,342 | 7/1990 | Steinemann | 607/116 |
| 4,989,617 | 2/1991 | Memberg et al. | 607/116 |
| 5,203,348 | 4/1993 | Dahl et al. | 128/642 |

Primary Examiner—Lee S. Cohen
Assistant Examiner—Marianne H. Parker
Attorney, Agent, or Firm—Steven M. Mitchell; Mark J. Meltzer; M. Elizabeth Bush

[57] ABSTRACT

An improved endocardial lead for electrocardial stimulation includes a sleeve that has a face surface. A conductor fitted into the sleeve, such that a distal end of the conductor passes completely through the sleeve, past the face surface, is electrically and mechanically connected to the face surface of the sleeve by mechanical means, e.g. crimping, and/or through the application of heat, e.g. welding or brazing. An electrode is integrated with the sleeve along an outer sleeve surface. A highly reliable, redundant joint is thereby provided between the sleeve and the conductor that secures the conductor against movement and therefore minimizes stress placed on the conductor, preventing fatigue to the conductor at the joint. A sleeve made in accordance with the present invention provides the narrowest and shortest possible conductor/electrode joint to minimize impact on the patient, while at the same time providing an endocardial lead that has excellent electrical properties, mechanical stability, and ease of manufacture, and that may be made from any desired material to thereby take advantage of new and/or improved materials.

28 Claims, 5 Drawing Sheets

ELECTRICAL CONNECTION FOR MEDICAL ELECTRICAL STIMULATION ELECTRODES

BACKGROUND OF THE INVENTION

1. Technical Field

The present invention relates to electrodes that are useful for medical applications. More particularly, the present invention relates to forming an electrically and mechanically reliable connection to a cardiac electrical stimulation and/or sensing electrode.

2. Description of the Prior Art

The use of electrical signals to stimulate or steady heart rhythm (pacing) or to restore heart rhythm when the muscle fibers of the heart undergo very rapid irregular contractions, which result in a lack of synchronism between the heartbeat and the pulse (defibrillation), is a well accepted, lifesaving medical technique. Pacing and defibrillation devices that produce these electrical signals typically consist of an electrical signal generator that is implanted inside a patient's body. The electrical signals produced by the signal generator are coupled to the patient's heart with an electrical lead that includes a conductor portion for carrying the electrical signal from the signal generator to the patient's heart and an electrode portion that makes actual electrical contact with the patient's heart.

Figure 1:
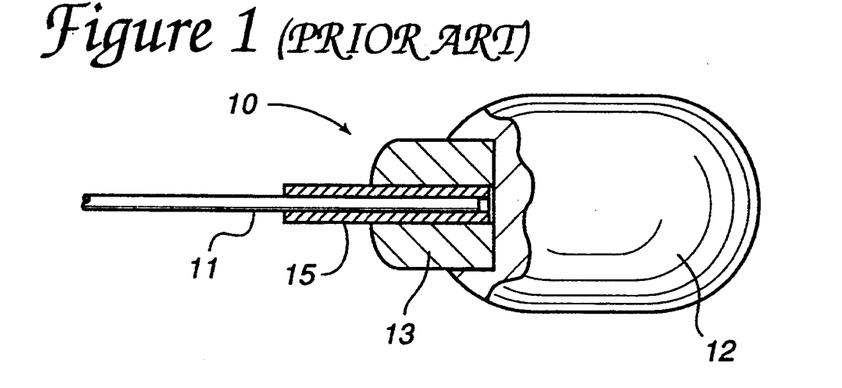
FIG. 1 is a partial sectional view of a prior art epicardial lead.

Leads for pacing and defibrillation are available for implantation around the heart, i.e. an epicardial lead. When such leads are used for pacing they are generally placed around the right ventricle or right atrium of the patient's heart, and when used for defibrillation they are generally placed around the right or left ventricle of the patient's heart. FIG. 1 shows a typical epicardial lead 10, in which a conductor 11 is joined to an electrode 12 at a joint 13 by crimping and/or welding onto a sleeve 15. Examples of epicardial leads are shown in U.S. Pat. Nos. 4,314,095, Device and Method for Making Electrical Contact, and 4,827,932, Implantable Defibrillation Electrodes.

Endocardial electrical stimulation leads are available for pervenous insertion to introduce the lead into the right ventricle or right atrium of the patient's heart for pacing, and into the patient's right ventricle or superior vena cava, which is slightly above the heart, for defibrillation (see FIGS. 2a and 2b, discussed below). Examples of endocardial leads are shown in U.S. Pat. Nos. 4,679,572, Low Threshold Cardiac Pacing Electrodes, 4,662,382, Pacemaker Lead with Enhanced Sensitivity, 4,458,695, Multipolar Electrode Assembly for Pacing Lead, 4,161,952, Wound Wire Catheter Cardioverting Electrode, and 4,844,099/4,784,161, Porous Pacemaker Electrode Tip Using a Porous Substrate.

Surgical procedures for implanting electrical leads into a patient's heart should be minimally intrusive. For this reason, endocardial leads, which are introduced into a patient's vein by means of a hollow tubular introducer, and anchored in the right ventricle by a fixation mechanism, or placed in the superior vena cava, coronary sinus, etc., are preferred over epicardial leads, which must be surgically implanted by opening the patient's chest. Although endocardial leads are less intrusive than epicardial leads, endocardial leads must pass through a vein and/or heart valve. It is therefore important to provide a lead with as small a diameter as possible, and thereby limit or eliminate entirely any damage to fragile veins or impairment of valve function that may be caused by the lead. It is also critical to provide a highly flexible lead, both for ease of positioning and for long term behavior of the lead within a patient's beating heart. Increased flexibility increases the fatigue life of the lead in the heart and thus reduces the likelihood of a lead failure.

Figure 2A:
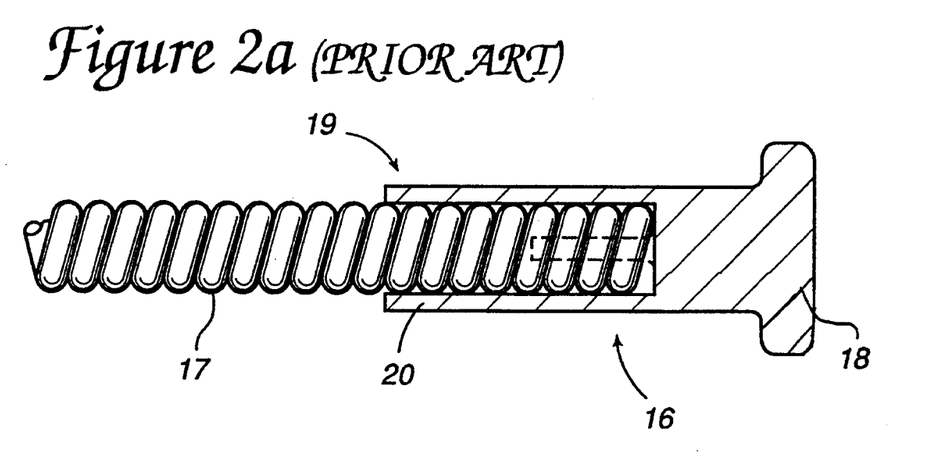
FIGS. 2a and 2b are partial sectional views of prior art endocardial leads.

In an endocardial lead 16, such as that shown in FIG. 2a, the conductor 17 and the electrode 18 are coupled at a joint 19 that must provide a low resistance electrical connection and a secure mechanical connection, while exhibiting a narrow profile to minimize intrusion of the lead into the patient's vein. Common practice is to mechanically join the conductor to the electrode at a sleeve portion 20 using a crimp or swage; and/or to form the joint with heat by brazing or welding.

Figure 2B:
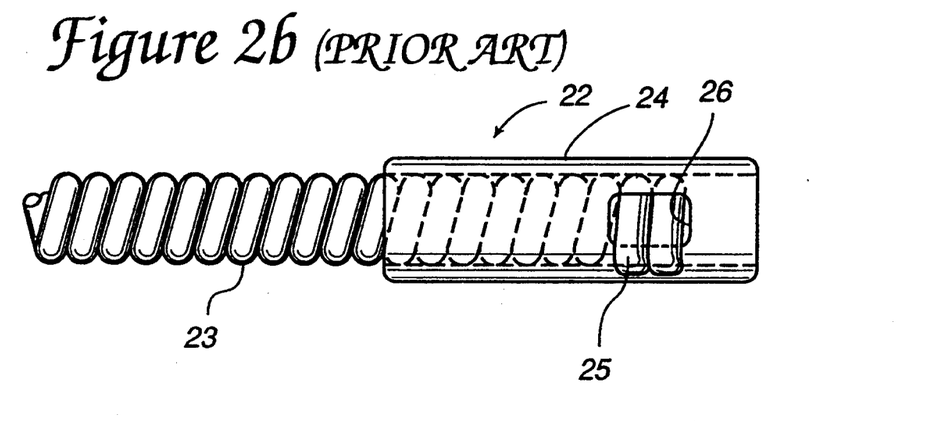

In FIG. 2b, an electrical stimulation lead 22 is shown having a coiled conductor 23 that is joined to a sleeve 24 by passing a portion of the distal end of the conductor through an aperture 26 formed in the side of the sleeve 24. The joint 25 between the conductor and the sleeve is completed by welding the distal end of the conductor to the outer sleeve surface. An electrode (not shown) may be joined to the sleeve surface as appropriate.

The joints shown in FIGS. 2a and 2b are not optimal for endocardial applications. In the joint shown in FIG. 2a, the sleeve must be both thick enough to provide sufficient strength to maintain a crimp bond, and the sleeve must have sufficient length to secure the crimp; while in the joint shown in FIG. 2b, the protrusion of the distal conductor end through the side of the electrode significantly increases the thickness of the electrode. The flexibility of each of these joints is reduced by the increased length needed when a multifilar coil is used as the conductor because a crimp or a weld must attach all of the wires of the coil in a row, thereby adding the diameter of the wire for each wire in the coil to the length of the joint.

Examples of various other joints having application in medical electrical stimulation electrodes are shown in U.S. Pat. Nos. 4,161,952, Wound Wire Catheter Cardioverting Electrode, 4,214,804, Press Fit Electrical Connection Apparatus, and 4,328,812, Ring Electrode for Pacing Lead.

Electrical joints in chronically implanted endocardial leads are subject to cyclical stresses, and should therefore be mechanically stable with respect to fatigue behavior. That is, due to the critical nature of the application to which the leads are put, a joint failure can have catastrophic results. Because the lead is implanted into a human body, it must also be both biocompatible (i.e. non-toxic) and corrosion resistant. The best conductors, for example silver and copper, are both toxic and subject to corrosion within the human body.

It would therefore be highly desirable to provide a lead for medical electrical stimulation applications having low electrical resistance, high mechanical and fatigue strength, biocompatibility, and high corrosion resistance, while minimizing intrusiveness of the lead into the patient's body, minimizing lead thickness, and maximizing flexibility.

SUMMARY OF THE INVENTION

The present invention provides an improved endocardial lead for electrocardial stimulation. In the preferred embodiment of the invention, the lead includes a sleeve which serves as an interface for joining a conductor to an electrode. An outer surface of the sleeve is adapted to support an electrode, which may be of any desired shape and which may be attached by mechanical or other means to the sleeve.

The sleeve also includes a sleeve face surface. A conductor is joined to the sleeve by passing a distal end of the conductor completely through the sleeve. The conductor is electrically and mechanically connected to the face surface of the sleeve by mechanical means, e.g. crimping, and/or through the application of heat, e.g. welding. The present invention therefore provides a highly reliable, redundant joint between the sleeve and the conductor that secures the conductor against movement and therefore minimizes stress placed on the conductor, preventing fatigue to the conductor at the joint.

A sleeve made in accordance with the present invention provides the narrowest possible conductor/electrode joint to minimize impact on the patient, while at the same time providing an endocardial lead that has excellent electrical properties, mechanical stability, and ease of manufacture, and that may be made from any desired material to thereby take advantage of new and-/or improved materials. Because the present invention is readily practiced with any specified conductor, such promising materials as drawn filled tubing, a low resistance conductor that exhibits excellent qualities of biocompatibility and corrosion resistance, but that has heretofore been difficult to use in the manufacture of endocardial leads, may be used to advantage.

BRIEF DESCRIPTION OF THE DRAWINGS

FIG. 3b is a partial sectional view of an endocardial lead according to a first preferred embodiment of the present invention;

DETAILED DESCRIPTION OF THE INVENTION

The present invention is best understood by referring to the Drawings in connection with review of this Description. The present invention provides an improved endocardial lead for electrocardial stimulation.

Figure 3A:
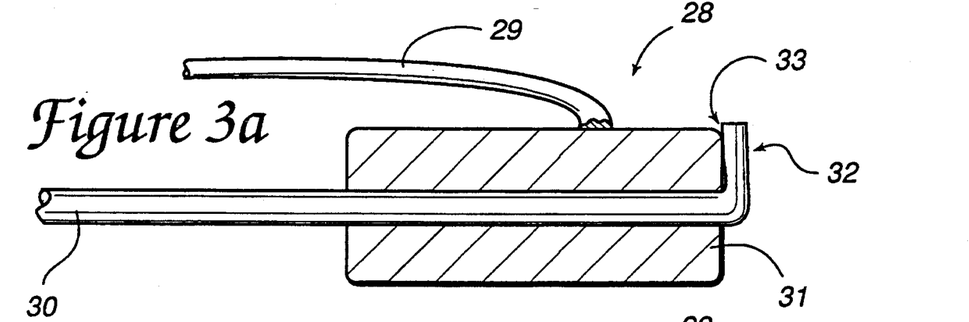
FIG. 3b is a partial sectional view of an endocardial lead according to another, equally preferred embodiment of the present invention.

FIG. 3a is a partial sectional view of an endocardial lead according to a first embodiment of the present invention. In the FIG., a lead 28 includes a conductor 30 that is joined to an electrode 29 at on elastically conductive sleeve 31. The conductor is fed into a first open end of the sleeve. A distal end 32 of the conductor 30 passes entirely through the sleeve and protrudes from a second open end of the sleeve in a face surface 33 of the sleeve. The conductor is bent back upon the outer face surface of the sleeve and joined to the sleeve by mechanical or other means to form a joint. Thus, the present invention joins a lead to an electrode in a way that provides support and stabilization of the conductor at the joint, while improving resistance of the joint to fatigue.

When a lead is formed in accordance with the teachings of the present invention, by positioning the conductor through the sleeve and then bending the end of the conductor onto the face of the sleeve, the resulting joint constrains the conductor in both the radial direction and in one axial direction before the actual mechanical joint is formed by welding, crimping, etc. This feature of the present invention facilitates formation of the mechanical joint by securing the conductor against movement relative to the sleeve while the weld or crimp is made. The resulting joint also provides a level of mechanical redundancy, i.e. the conductor is secured in the present invention by both the initial axial and radial constraint of the sleeve, and by the mechanical attachment of the conductor to the sleeve, e.g. by crimping. In this way, the invention produces a stronger, more secure connection between the conductor and the sleeve (and therefore between the conductor and the electrode).

The present invention also allows the narrowest possible joint between a conductor and an electrode. That is, the actual thickness of the sleeve is very small relative to that of the conductor. Therefore, a joint may be formed in accordance with the present invention that is not noticeably wider than the conductor itself (and, in some embodiments, may be narrower than the conductor). Additionally, the sleeve of the present invention need not be very long because the actual joint is formed at the face of the sleeve. Thus, the flexibility of the lead is not impaired by a long, rigid joint, as is the case in prior art leads. In this way, the present invention allows a lead to be produced that is minimally intrusive, both in length and in thickness. Additionally, as finer, thinner materials are introduced, the present invention is readily adapted for use with such materials.

Figures 4A, 4B:
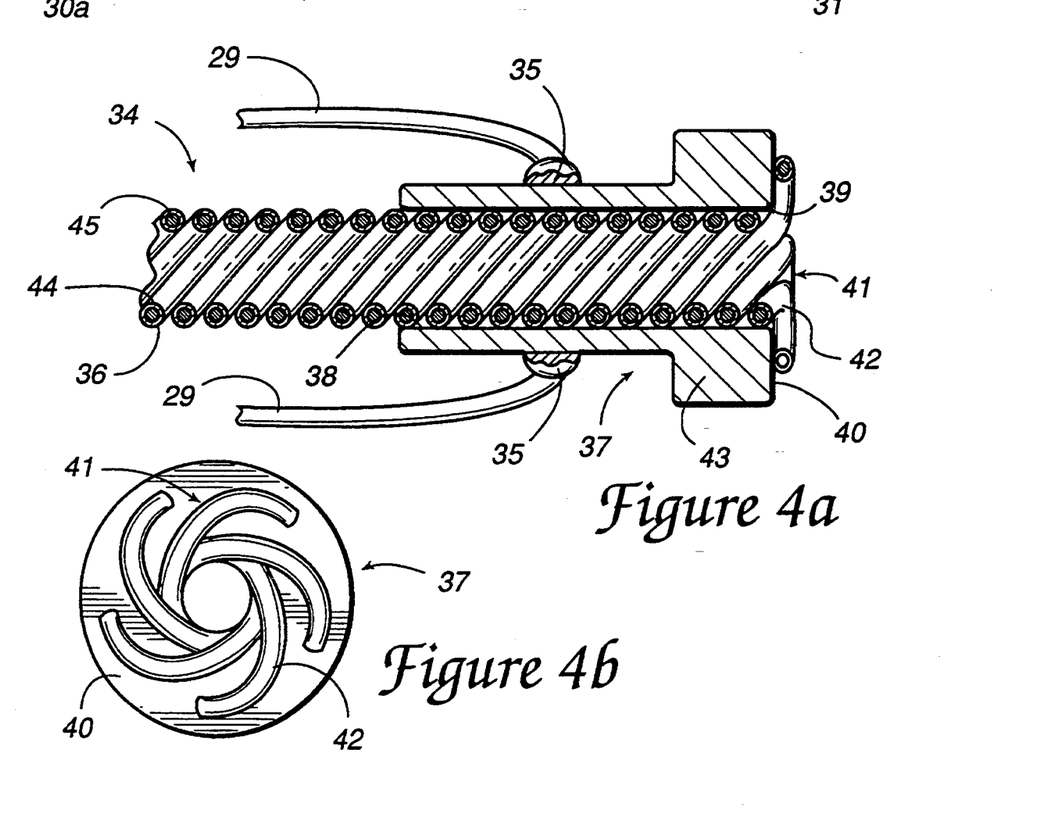
FIGS. 4a and 4b provide a partial sectional view and a front surface view of an endocardial lead according to another embodiment of the present invention.

FIG. 4a provides a partial sectional view, and FIG. 4b provides a front surface view, of an lead according to another, equally preferred embodiment of the present invention. As shown in the FIGS., a lead 34 includes a conductor 36 that is electrically and mechanically connected by a sleeve 37 to an electrode 29 at bond point 35. The sleeve has a first opening 38 in a first end and it has a face surface 40 at its other end. A second sleeve opening 39 is formed through the sleeve face surface 40. The electrode may be joined at any desired bond point 35 along the outer intermediate surface of the sleeve, the intermediate outer surface lying between the two ends of the sleeve.

In one embodiment of the invention, the first opening 38 of the sleeve may be inwardly tapered or countersunk to facilitate assembly of the lead and prevent the sleeve from cutting or abrading the conductor when the lead is flexed, for example, when the patient's heart is beating. Likewise, second sleeve opening 39 may be tapered or countersunk to facilitate assembly and to avoid a sharp edge over which the distal end 42 of conductor 36 must be bent.

In the present invention, the conductor may be formed of any selected material that provides a low resistance, biocompatible, corrosion resistant path from a signal generator, such as a pacer or a defibrillator, to an electrode. Thus, the present invention allows the use of many different conductor materials, including solid conductors, stranded conductors, etc.

In one embodiment of the present invention, a preferred conductor material is drawn filled tube, such as is supplied by Fort Wayne Metals of Fort Wayne, Ind. A conductor 36 made of drawn filled tubing is preferably formed as a multifilar coil, i.e. a spiral coil wound of at least two or more parallel conductors. Providing a conductor in the form of a multifilar coil in the present invention increases conductivity and redundancy, both in the conductor coil itself and at the joint between the conductor and the sleeve. That is, because several conductors are wound in parallel, the conductor provides significant redundancy and increased conductivity. In the intended application of the present invention, where failure of a single strand conductor could have serious consequences, i.e. in an electrocardial lead, such redundancy is essential.

Drawn filled tubing (or "DFT") provides a very fine, flexible, hollow tube 44 formed of a nontoxic, corrosion resistant material, such as stainless steel, or MP35N, which is an alloy made up of about 35% cobalt, 35% nickel, 20% chromium, and 10% molybdenum. Multiple strands of DFT are readily wound in parallel to form a multifilar coil. The hollow inner portion of DFT is filled with a highly conductive material, such as silver 45. This structure therefore provides the tensile strength, corrosion resistance, fatigue resistance, and biocompatibility of MP35N or stainless steel with the high conductivity of silver.

In the preferred embodiment of the present invention, a portion of the silver in each drawn filled tubing conductor is etched away at the distal end of the conductor where the conductor is joined to the sleeve. This step minimizes the possibility of leaching the toxic silver filling of the DFT conductor. The distal end of the conductor is then a hollow tube which is flattened prior to joining the conductor to the sleeve. This step of flattening is also useful to help prevent leaching of silver from the DFT conductor. However, because welding the conductor to the sleeve also closes the end of the tubing, the hollow distal end of the conductor need not be flattened prior to welding in all embodiments of the invention. The step of etching away the silver filling from the distal end of the conductor also ensures that only the tubing material is joined to the sleeve and not silver. This provides a more reliable joint. Alternatively, the silver may be etched away from the joint after the tubing is welded to the sleeve.

The preferred etching method involves the use of a solution, such as a mixture of hydrogen peroxide and ammonia solution, or a mixture of concentrated nitric acid and water. The rate of etch can be accelerated by ultrasonic agitation. The etch rate can also be accelerated by heating the solution. Other etching solutions, such as sulfuric acid or cyanide solutions can be used, but are more difficult to handle.

If the outer tube is made of a chromium bearing alloy, it is advantageous to use an oxidizing solution for etching the silver to maintain passivity of the outer tube.

EXAMPLE 1

Using a solution composed of:
1 part hydrogen peroxide (30%)
1 part ammonia (27%)

The samples are immersed for a period of 15 minutes in an ultrasonic bath. Cleaning of the samples is done in ultrasonic baths of water and isopropanol for a period of 10 minutes each.

EXAMPLE 2

Using a solution composed of:
1 part concentrated nitric acid
1 part deionized water The samples are immersed for a period of 1 hour in an ultrasonic bath. Cleaning is done in ultrasonic baths of water and isopropanol for a period of 10 minutes each.

The present invention also allows the use of Pt/10 Ir electrodes, which are highly conductive, are biocompatible, and which exhibit excellent corrosion and fatigue resistance. In one embodiment of the invention, an electrode formed of Pt/10 Ir material may be joined to a Pt/10 Ir sleeve. This arrangement simplifies joining the electrode to the sleeve, e.g. by welding, and minimizes the possibility of corrosion at the electrode/sleeve joint due to the electrolytic action often encountered when dissimilar metals are joined together.

The present invention allows the lead to be constructed of matched materials or dissimilar materials. For example, in one embodiment of the invention the sleeve and the conductor may both be made of MP35N. In other embodiments of the invention, the electrode and the conductor may each be made of different materials that are difficult to join by welding.

Thus, in one embodiment of the invention, the sleeve may be made of a material that is readily welded to one or the other of the electrode and conductor materials, and that is readily crimped to the other of the electrode and conductor materials. In another embodiment of the invention, the sleeve may be made of a material that may be welded to both the electrode material and the conductor material. In this embodiment of the invention, the sleeve serves as an intermediary or interface material.

An important aspect of the present invention is that the connection between the electrode and the sleeve may be a weld, braze, or conductive polymer connection, or some combination thereof. Joining the electrode to the sleeve in this way allows the use of a very short, thin sleeve that does not contribute significantly to overall lead length or diameter. This feature of the present invention is very important in applications where the lead must be inserted through very small and fragile blood vessels. In contrast, a direct connection between the conductor and the electrode, as practiced in the prior art, requires sufficient length and thickness to support the joint.

It should be appreciated that the present invention may be practiced to provide a lead in which the sleeve outer diameter is greater than, equal to, or less than the outer diameter of the conductor. The actual sleeve outer diameter chosen is a function of the application to which the lead is put and the materials from which the lead is formed.

Figure 3B:
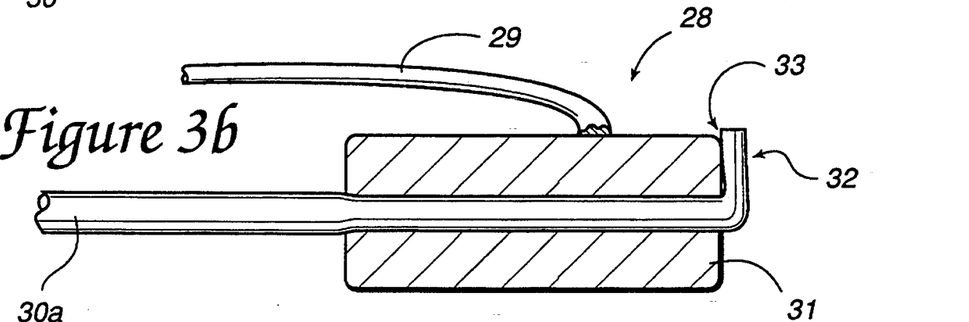

For example, in the embodiment of the invention shown in FIG. 3b, the sleeve 31 has an inner diameter that is smaller than the outer diameter of the conductor 30a, and which therefore provides an interference (friction) fit between the sleeve and the conductor. Such fit enhances stability at the joint during assembly of the lead, while providing redundancy to the joint by pressing the conductor into electrical and mechanical contact against the sleeve wall. This mechanical fitting is sufficient to carry current through the joint even if the weld, crimp, braze, etc. of the conductor to the sleeve were to fail.

The actual formation of the joint between the sleeve, the electrode, and the conductor in the present invention may be accomplished by any of several known techniques. In the preferred embodiment of the invention, the electrode is joined to the outer body of the sleeve by a resistance weld. Formation of the electrode/sleeve joint may be facilitated by using similar materials for each of the sleeve and electrode. Resistance welding is preferred in making such joint because it allows minimum sleeve thickness. In contrast, a crimp joint requires sufficient bulk to physically hold the electrode to the sleeve. This bulk adds both length and thickness to the joint and is, therefore, not preferred for the electrode/sleeve joint.

A resistance weld may also be used to join the conductor to the sleeve. When forming the conductor/sleeve joint in this way, a resistance weld joint also dispenses with the requirement of a support tube or pin to prevent the conductor from collapsing when compressive force is applied to the sleeve during the crimping operation. It should be appreciated that the present invention may nonetheless be practiced using a crimp to form either or both of the conductor/sleeve and electrode/sleeve joints, and that a joint may be formed using both a weld and a crimp, etc. The conductor may be joined to the sleeve either at the sleeve face surface or along a sleeve outer surface.

In another embodiment of the invention, the sleeve includes a shoulder that is arranged to provide more surface area for a welding or crimping joint, without increasing the lead diameter beyond that needed to join the electrode to the sleeve. The shoulder also provides a surface to which a molded or glued separate portion of a sleeve assembly may be mechanically attached; and provides a firm seat for a welding electrode when the conductor is resistance welded to the face of the sleeve. The shoulder also provides a physical barrier at the point where the electrode is joined to the sleeve. This barrier serves to shield the electrode.

Another embodiment of the invention provides an annular recess formed in the outer face surface of the sleeve. Providing such recess allows the conductor to be joined to the sleeve by laser welding and is also useful for braze joints, where it is desirable to contain the liquid metal produced during the welding process.

In the embodiment shown in FIGS. 4a and 4b, the sleeve 37 includes a shoulder 43. The distal end 42 of the conductor is shown inserted into the first open end 38 of the sleeve and it is shown exiting the sleeve through the second sleeve open end 39, which is formed in the outer face surface 40 of the sleeve. The distal end of the conductor is fanned out and bent onto the face of the sleeve, to which it is then bonded by welding, brazing, conductive polymers, etc. to form an electrical and mechanical joint 41 between the sleeve and the conductor.

Figure 5A:
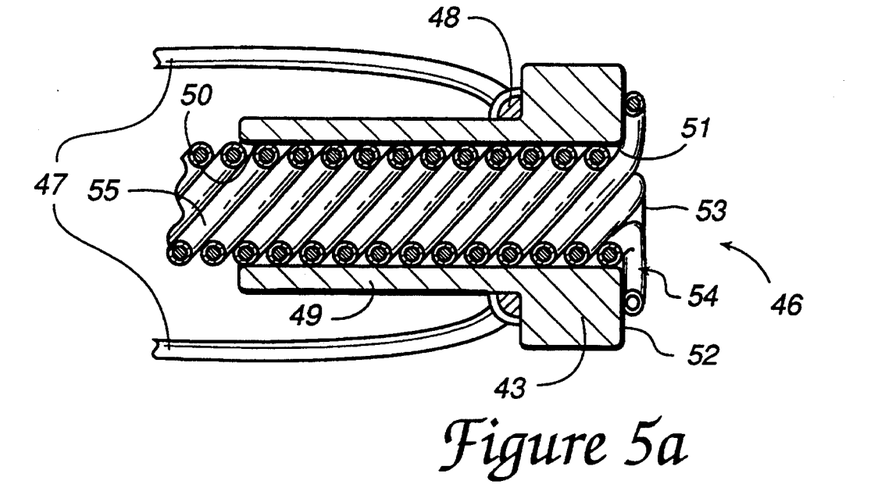
FIG. 5a is a partial sectional view of an endocardial lead according to another embodiment of the present invention.

FIG. 5a is a partial sectional view of an endocardial lead according to another embodiment of the present invention. In the FIG., a lead 46 includes a conductor 55 that is coupled to an electrode 47 by a sleeve 49. A distal end 53 of the conductor 55 is inserted into a first open end 50 of the sleeve; a portion of the end of the conductor exits the sleeve through a second open end 51. The distal end of the conductor is then bent against a face surface 52 of the sleeve, where it is bonded to the sleeve to form a joint 54. The electrode 47 is bonded to both the outer surface of the cylindrical portion of the sleeve and to the base of the shoulder 43 of the sleeve.

Figure 5B:
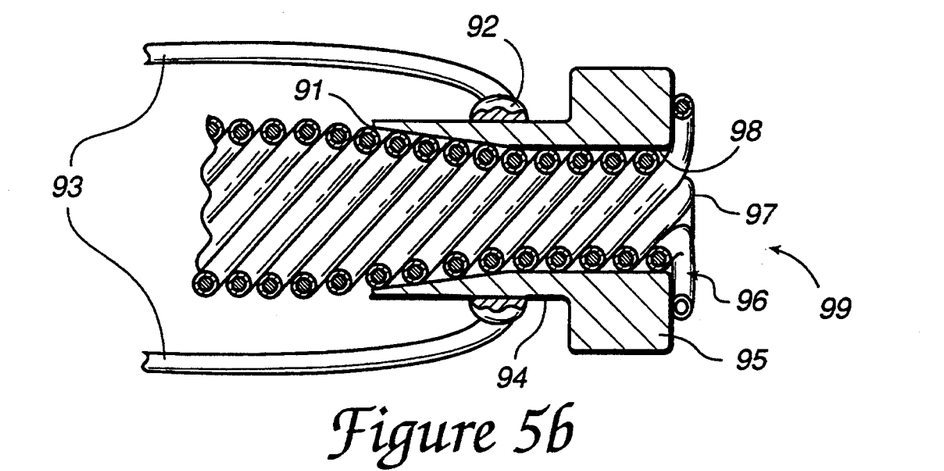
FIG. 5b is a partial sectional view of an endocardial lead according to another, equally preferred embodiment of the present invention.

FIG. 5b is a partial sectional view of an endocardial lead according to another, equally preferred embodiment of the present invention in which a conductor 90 has an outer diameter that is greater than the outer diameter of a sleeve 94 into which the conductor is inserted. In the FIG., a lead 99 includes a conductor 90 that is coupled to an electrode 93 by the sleeve 94. A distal end 97 of the conductor 90 is inserted into a first open end 91 of the sleeve. The conductor 90 may first be compressed prior to insertion into the sleeve 94. A portion of the end of the conductor exits the sleeve through a second open end 98. The distal end of the conductor is then bent against a face surface 95 of the sleeve, where it is bonded to the sleeve to form a joint 97. The electrode 93 may be bonded to an outer surface of the sleeve at any desired bond point 92 along said surface.

Figure 5C:
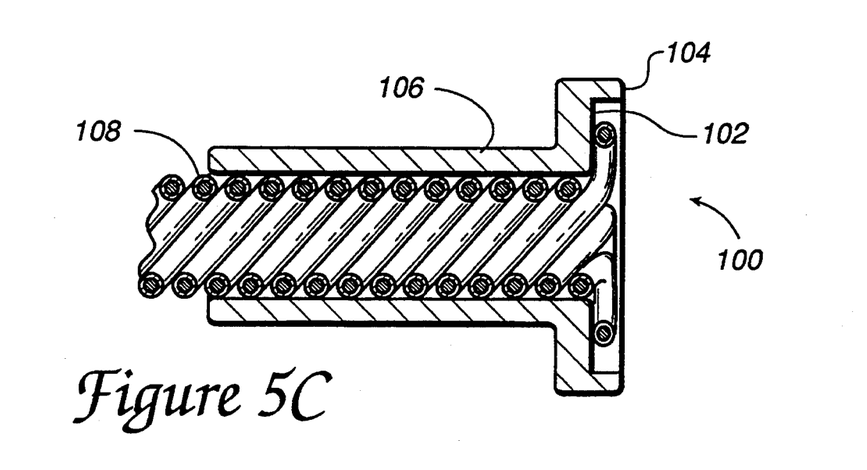
FIG. 5c is a partial sectional view of an endocardial lead according to a further embodiment of the present invention.

FIG. 5c is a partial view of an endocardial lead 100 according to a further embodiment of the present invention, which provides an annular recess 102 formed in the outer face surface 104 of the sleeve 106. Providing such recess allows the conductor 108 to be joined to the sleeve by laser welding and is also useful for braze joints, where it is desirable to contain the liquid metal produced during the welding process.

Figure 6A:
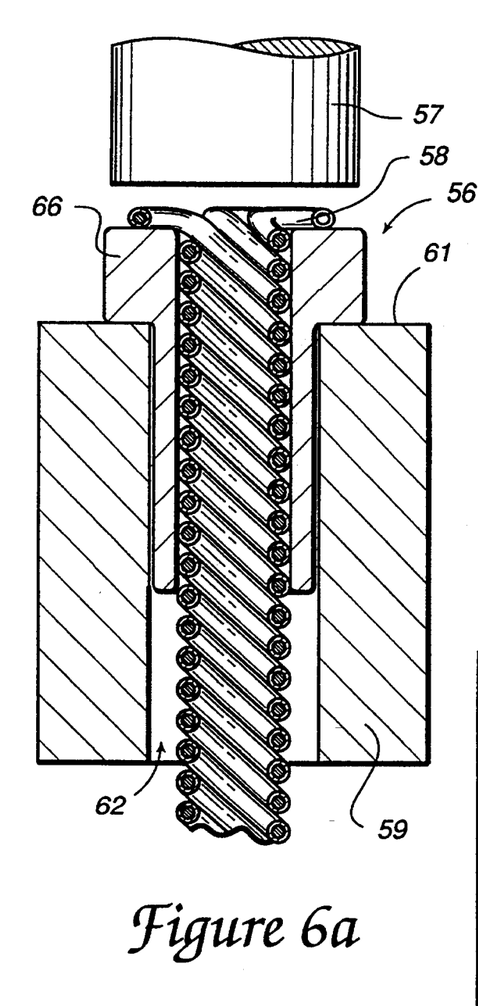
FIGS. 6a and 6b provide a partial sectional view of an endocardial lead showing alternate methods of resistance welding a conductor to a sleeve according to the present invention.
Figure 6B:
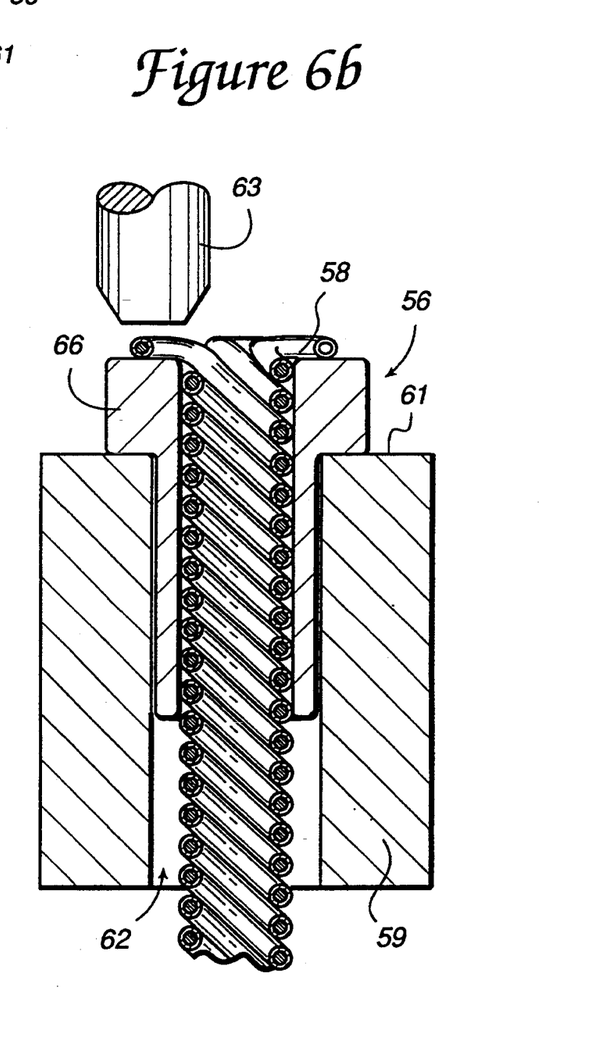

FIGS. 6a and 6b provide a partial sectional view of an endocardial lead showing alternate methods of employing resistance welding to form a joint between a conductor and a sleeve according to the present invention. In the embodiment of the invention shown in FIG. 6a, the lead 56 includes a sleeve 66 that is fitted into an opening 62 formed in a first resistance welding electrode 59; the sleeve has a shoulder that abuts an upper surface 61 of the first resistance welding electrode 59 and that therefore maintains the sleeve in place during welding. A second resistance welding electrode 57 is brought to bear on an upper sleeve surface to weld a distal conductor end to a front outer sleeve surface and thus form a joint 58. Thus, in the embodiment of the invention shown in FIG. 6a, all conductor ends are joined to a sleeve outer face surface at the same time.

An alternative embodiment of the invention is shown in FIG. 6b, in which a second resistance welding electrode 63 is configured to join one conductor end at a time to the sleeve outer face sleeve surface.

Figures 7, 8A, 8B:
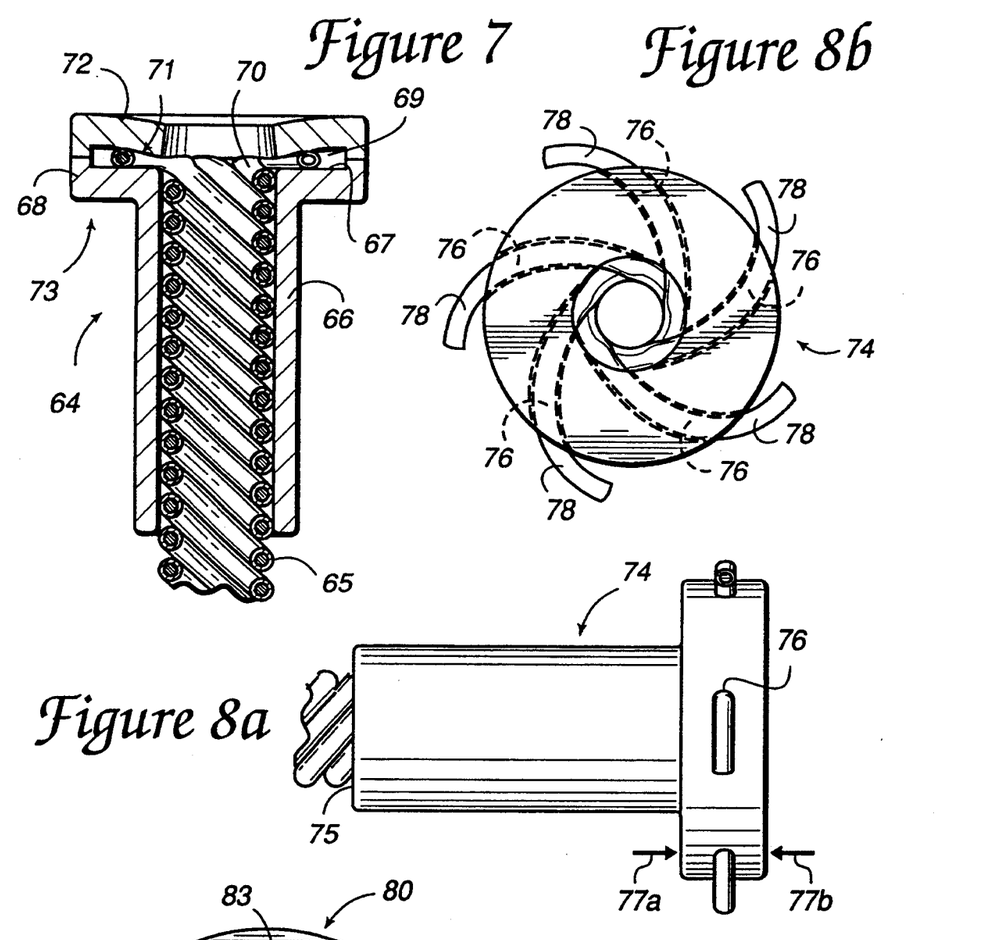
FIG. 7 is a sectional view of an endocardial lead showing a method of crimping a conductor to a sleeve according to the present invention.
FIGS. 8a and 8b are a side view and a front surface view of an endocardial lead showing another method of crimping a conductor to a sleeve according to the present invention.

FIG. 7 is a sectional view of an endocardial lead showing a method that is useful for crimping a conductor to a sleeve according to the present invention. In the FIG., a lead 64 includes a multifilar coiled conductor 65 that is inserted into an open end of a sleeve 66. The distal ends 70 of each conductor in the multifilar coil are bent against an inner sleeve surface 67 in a base sleeve portion 68. A cap sleeve portion 72 is then joined to the sleeve at the inner sleeve surface, e.g. by welding, brazing, conductive polymers, etc., to form a cavity 69. Compressive pressure is applied to the cap portion of the sleeve to collapse the cavity and mechanically and electrically secure the distal end of each conductor to the sleeve at a joint 71. A shoulder 73 may be provided on the sleeve which is used as a seat for holding the sleeve against movement during crimping.

FIG. 8a is a side view, and FIG. 8b is a front surface view, of an endocardial lead showing another method that is useful for crimping a conductor to a sleeve according to the present invention. In the FIGS., a sleeve 74 has an open end 75 that receives the distal conductor ends 78 of a multifilar coil. A plurality of apertures 76 are formed in a shoulder portion of the sleeve through which the distal conductor ends are fed. A crimping force is applied to the shoulder, as shown by lines 77a, 77b, to complete a mechanical and electrical bond between the sleeve and the conductors. The outer surface of the sleeve may then be polished to remove any portion of the conductors that protrudes beyond the outer surface of the sleeve.

Figure 9:
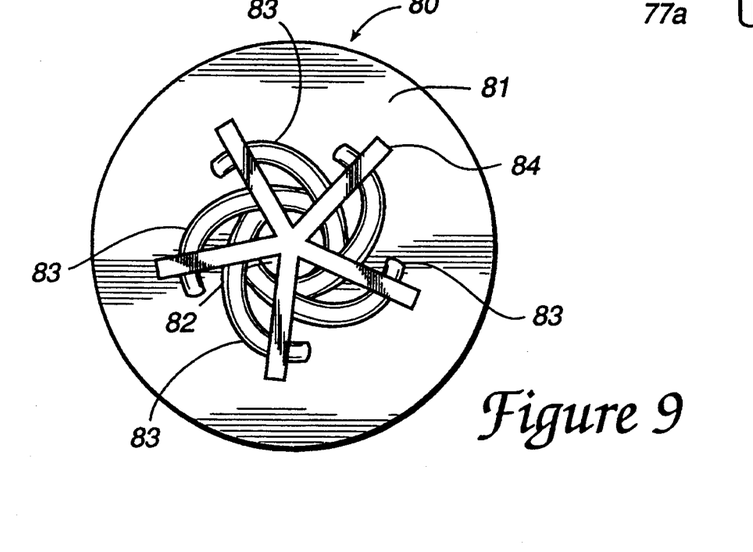
FIG. 9 is a front surface view of an endocardial lead showing a method for resistance welding a conductor to a sleeve according to the present invention.

FIG. 9 is a front surface view of an endocardial lead showing a method that is useful for resistance welding a conductor to a sleeve according to the present invention. In the FIG., a sleeve 80 has a face surface 81 through which an aperture 82 is formed. The distal conductor ends 83 of a multifilar coil are threaded through the aperture, where they are bent back against the face surface 81 of the sleeve. A resistance welding electrode 84 is brought to bear on each of the individual conductors to form a joint between each of the conductors and the face surface of the sleeve.

Although the invention is described herein with reference to the preferred embodiment, one skilled in the art will readily appreciate that other applications may be substituted for those set forth herein without departing from the spirit and scope of the present invention. For example, one embodiment of the present invention provides a coiled conductor that defines a hollow inner channel or pathway that may be used as a lumen for a stylet, for an inner insulator and conductor, for a fiber optic strand, or for a drug delivery conduit, etc. Accordingly, the invention should only be limited by the claims included below.

We claim:

1. An endocardial lead, comprising:
   a hollow tubular, electrically conductive sleeve having a first open end for receiving a conductor, and having a second open end including an outer face surface;
   an electrode, electrically and mechanically integrated with an outer intermediate surface of said sleeve between said first and second ends; and
   a conductor, fitted into said sleeve through said first open sleeve end, such that a distal end of the conductor passes through the sleeve to the face surface of the sleeve, where the conductor is electrically and mechanically connected to the sleeve.

2. The lead of claim 1, wherein said sleeve has a central axis and further comprises:
   a shoulder extending along a length of said sleeve parallel to said sleeve axis.

3. The lead of claim 1, wherein said conductor is formed of a composite wire, comprising at least a first metal and a second metal, said first metal completely surrounding said second metal along said wire.

4. The lead of claim 3, wherein said conductor is a drawn filled tubing which comprises:
   an outer tubing formed of a chromium bearing alloy; and
   a silver filling.

5. The lead of claim 4, wherein said conductor is configured as a multifilar coil, each filament of which comprises drawn filled tubing having a distal end from which the silver filling has been removed.

6. The lead of claim 4, wherein said chromium bearing alloy is MP35N.

7. The lead of claim 3, wherein said conductor is a drawn filled tubing which comprises:
   a stainless steel outer tubing; and
   a silver filling.

8. The lead of claim 3, wherein said conductor is a multifilar coil, each conductor of which is connected to said sleeve such that said second metal is not exposed.

9. The lead of claim 1, wherein said sleeve is formed of a platinum/iridium alloy.

10. The lead of claim 1, wherein said electrode is formed of a platinum/iridium alloy.

11. The lead of claim 1, wherein said conductor is a coil.

12. The lead of claim 1, wherein said conductor is a multifilar coil.

13. The lead of claim 1, wherein said sleeve has an outer diameter dimension that is less than an outer diameter dimension of said conductor.

14. The lead of claim 1, wherein said sleeve has an outer diameter dimension that is equal to an outer diameter dimension of said conductor.

15. The lead of claim 1, wherein said sleeve has an outer diameter dimension that is greater than an outer diameter dimension of said conductor.

16. The lead of claim 1, wherein said conductor is resistance welded to said sleeve face surface.

17. The lead of claim 1, wherein said sleeve first open end includes a tapered inner sleeve surface.

18. The lead of claim 1, wherein said second sleeve open end includes a tapered inner sleeve surface.

19. The lead of claim 1, wherein said electrode is resistance welded to said sleeve.

20. The lead of claim 19, wherein said electrode is resistance welded to a sleeve outer surface and to a sleeve shoulder.

21. The lead of claim 1, wherein said conductor is crimped to said sleeve.

22. The lead of claim 1, wherein said conductor defines a hollow inner channel, said channel providing a pathway that is parallel to a conductor pathway.

23. The lead of claim 1, wherein said sleeve includes a shoulder portion having an outer shoulder surface with at least one aperture formed therethrough, said aperture adapted to receive said distal conductor end.

24. The lead of claim 1, wherein said sleeve is formed of MP35N.

25. The lead of claim 24, wherein said conductor is formed of MP35N.

26. The lead of claim 1, wherein said outer face surface includes an annular recess formed therein.

27. An endocardial lead, comprising:
   an electrically conductive sleeve having a central axis and an open end for receiving a conductor;
   an electrode, electrically and mechanically connected to a surface of said sleeve; and
   said conductor having an end fitted into said sleeve through said open end, and electrically and mechanically connected to said sleeve in a plane perpendicular to said sleeve axis.

28. The endocardial lead of claim 27, wherein said conductor is a multifilar coil, and said conductor end comprises an end of each wire of said multifilar coil, said wire ends being connected to said sleeve in said perpendicular plane.

* * * * *